United States Patent [19]
Zakikhani et al.

[11] Patent Number: 5,980,776
[45] Date of Patent: *Nov. 9, 1999

[54] PHOSPHONIC ACID POLYMERS

[75] Inventors: Mohsen Zakikhani, Harborne; David Robert Edward Walker, Hanburg; Peter David Hasling, Highley; Alan Craig Smith, Bedworth; Keith Philip Davis, West Midlands, all of United Kingdom

[73] Assignee: Albright & Wilson UK Limited, West Midlands, United Kingdom

[ * ] Notice: This patent issued on a continued prosecution application filed under 37 CFR 1.53(d), and is subject to the twenty year patent term provisions of 35 U.S.C. 154(a)(2).

[21] Appl. No.: 08/937,070

[22] Filed: Sep. 24, 1997

Related U.S. Application Data

[62] Division of application No. 08/758,354, Dec. 3, 1996, abandoned.

[30] Foreign Application Priority Data

Dec. 21, 1995 [GB] United Kingdom ........... 95262010
Jul. 5, 1996 [GB] United Kingdom ........... 9614186

[51] Int. Cl.$^6$ ................................ C02F 5/14
[52] U.S. Cl. .............. 252/175; 210/681; 210/688; 210/687; 252/180; 521/38; 526/278

[58] Field of Search ............... 526/278; 210/688, 210/681, 687; 252/175, 180

[56] References Cited

U.S. PATENT DOCUMENTS

| | | | |
|---|---|---|---|
| 3,544,509 | 12/1970 | Carroll | 526/278 |
| 3,576,793 | 4/1971 | Carroll | 526/278 |
| 5,091,491 | 2/1992 | Quach | 526/278 |
| 5,281,631 | 1/1994 | Horwitz | 521/38 |
| 5,332,531 | 7/1994 | Horwitz et al. . | |
| 5,449,462 | 9/1995 | Horwitz | 210/682 |
| 5,539,003 | 7/1996 | Horwitz | 521/33 |

FOREIGN PATENT DOCUMENTS

| | | |
|---|---|---|
| 856193 | 11/1970 | Canada . |
| 1204967 | 9/1970 | United Kingdom . |

*Primary Examiner*—Fred Zitomer
*Attorney, Agent, or Firm*—Frishauf, Holtz, Goodman, Langer & Chick, P.C.

[57] ABSTRACT

Phosphonic acid polymers are prepared from di- or polyphosphonic acids having one or more unsaturated C=C bonds (e.g. vinylidene-1,1-diphosphonic acid), either as homopolymers or as higher polymers with at least one further compound having unsaturated C=C bonds (e.g. acrylic acid). The polymers can be used as, or in connection with, flame-retardants, corrosion inhibitors, coatings, cements and ion exchange resins.

25 Claims, No Drawings

PHOSPHONIC ACID POLYMERS

This application is a Division of application Ser. No. 08/758,354, filed Dec. 3, 1996, now abandoned.

This invention relates to phosphonic acid polymers and in particular to polymers derived from di- or poly-phosphonic acids, or salts of such acids, containing one or more unsaturated carbon-to-carbon bonds.

This invention also relates to the use of the aforesaid polymers as, or in connection with, inter alia, flame-retardants, adhesion promoters, corrosion inhibitors, scale inhibitors, lithographic additives, coatings, films, printing inks, ion exchange resins, dispersing agents, flocculating agents, dental cements, bone cements and mouth-wash chemicals.

This invention further relates to the use of the aforesaid polymers as, or in connection with, scale inhibitors, corrosion inhibitors or ion-exchangers for the treatment of aqueous liquids.

The specification of GB 1204967 discloses the preparation of certain phosphonic acid polymers and mentions their possible use in connection with aqueous, highly alkaline (pH 11 or greater) liquids as corrosion inhibitors.

We have found that the inhibition of scale formation, particularly the inhibition of barium sulphate scale formation, in aqueous liquids of pH as low as 4, is unexpectedly achieved by means of phosphonic acid polymers of the type hereinafter described.

Accordingly the present invention provides a polymer derived from a di- or poly-phosphonic acid containing one or more unsaturated carbon-to-carbon bonds, or from a salt of said phosphonic acid.

In a first preferred embodiment of the present invention, the polymer is a homopolymer of a di-phosphonic acid containing one or more unsaturated carbon-to-carbon bonds, or of a salt of said phosphonic acid.

In a second preferred embodiment of the present invention, the polymer is a polymer of a di-phosphonic acid containing one or more unsaturated carbon-to-carbon bonds, or of a salt of said phosphonic acid, with at least one further compound containing one or more unsaturated carbon-to-carbon bonds. A specific embodiment of the invention described in the immediately-preceding paragraph consists of a terpolymer of a diphosphonic acid containing one or more unsaturated carbon-to-carbon bonds, or a salt of said phosphonic acid, with two further compounds, each containing one or more unsaturated carbon-to-carbon bonds.

The di-phosphonic acid may be vinylidene-1,1-diphosphonic acid or a mono, di-, tri- or tetra-alkali metal salt of that acid, for example the mono-, di-, tri- or tetra-sodium salt.

The further compound containing one or more unsaturated carbon-to-carbon bonds may be an unsaturated carboxylic acid or a fully or partly neutralised metal salt thereof, such as the mono- or di-sodium salt. Alternatively, the further compound may be a mono- or polyfunctional sulphonic acid or a fully or partly neutralised salt thereof.

Suitable examples of sulphonic acids for use in connection with the present invention include vinyl sulphonic acid (VSA), acrylamido methyl propane sulphonic acid (AMPS) and fully or partly neutralised salts of either said acid.

The molar ratio of vinylidene-1,1-diphosphonic acid to VSA or AMPS may be in the range 1:99 to 99:1, for example 50:50, 33:66 or 10:90.

Other examples of the further compounds referred to hereinabove include vinyl phosphonic acid, acrylic acid, methacrylic acid, maleic acid, the fully or partly neutralised salts of said acids, and acylonitrile.

The present invention further provides the following polymers per se:

(i) a homopolymer consisting essentially of poly (vinylidene-1,1-di-phosphonic acid);
(ii) a homopolymer consisting essentially of the mono-, di-, tri- or tetra-sodium salt of poly(vinylidene-1,1-di-phosphonic acid);
(iii) A copolymer consisting essentially of vinylidene-1, 1-di-phosphonic acid and acrylic acid;
(iv) A copolymer consisting essentially of the sodium salt of vinylidene-1,1-di-phosphonic acid and acrylic acid.
(v) A copolymer consisting essentially of vinylidene-1,1-diphosphonic acid and maleic acid;
(vi) A copolymer consisting essentially of vinylidene-1, 1-diphosphonic acid and mono-sodium maleate;
(vii) A cross-linked copolymer consisting essentially of vinylidene-1,1-di-phosphonic acid and acrylic acid.

The present invention yet further provides a polymer of vinylidene-1,1-diphosphonic acid, vinyl sulphonic acid and a compound selected from vinyl phosphonic acid, acrylic acid, methacrylic acid, maleic acid, the fully or partly neutralised salts of said acids, and acrylonitrile.

The present invention additionally provides the use of a polymer according to either of the two preferred embodiments hereinabove described as, or in connection with a flame retardant, an adhesion promoter, a corrosion inhibitor, a scale inhibitor, a lithographic additive, a coating, a film, a printing ink, an ion exchange resin, a dispersing agent, a flocculating agent, a dental cement, a bone cement or a mouth-wash chemical.

The present invention still further provides the use as, or in connection with, a scale inhibitor, a corrosion inhibitor or an ion-exchanger for the treatment of an aqueous liquid having a pH of up to 8.5, of a polymer derived from a di- or poly-phosphonic acid containing one or more unsaturated carbon-to-carbon bonds or of a polymer derived from a salt of such an acid.

For example, the aqueous liquid may have a pH of up to 8.0, suitably in the range 1.0 to 7.0 and especially in the range 3.5 to 6.5.

In a third embodiment of the invention, the polymers may be used to inhibit the formation of insoluble divalent or trivalent metal salts in the aqueous liquid, thereby inhibiting the formation of scale.

The scale may be, for example, barium sulphate or calcium carbonate scale. Alternatively, the scale may comprise one or more sulphates of calcium, strontium, radium or lead.

In a fourth embodiment of the invention, the polymers may be used to inhibit corrosive action of the aqueous liquid on a metal (e.g. aluminium or copper) surface.

In a fifth embodiment, the polymers may be used as, or in connection with, ion-exchangers for the treatment of aqueous liquids containing rare earth (e.g. lanthanide or actinide) metal ions in solution.

Polymers according to the present invention may also be used as pharmaceutical intermediates, solid-suspending additives, lubricant additives, paint additives or solid-phase coupling agents.

The present invention will be illustrated by way of the following Examples:

EXAMPLE 1

Synthesis of poly(vinylidene-1,1-diphosphonic acid) (PVDPA)

A resin pot fitted with a thermometer, a condenser, a nitrogen outlet, a stirrer, an addition funnel, and a nitrogen inlet was flushed with nitrogen for 30 minutes.

Vinylidene-1,1-diphosphonic acid (10 grams), potassium persulphate (2 grams), and deionised water (40 grams) were added and the reaction vessel was heated in an oil bath set at 110° C. until the reflux temperature was attained. The reaction mixture was maintained at reflux for 6 hours.

The resultant solution was found to consist essentially of a homopolymer of VDPA, as shown by $^{31}$P N.M.R.

EXAMPLE 2

Synthesis of poly(vinylidene-1,1-diphosphonic acid-co-acrylic acid)

A resin pot fitted with a thermometer, a condenser, a nitrogen outlet, a stirrer, an addition funnel, and a nitrogen inlet with flushed with nitrogen for 30 minutes.

Vinylidene-1,1-diphosphonic acid (6.8 grams), and deionised water (40 grams) were added to the vessel. The reaction vessel was heated in an oil bath set at 110° C. until the reflux temperature was attained. The contents were maintained at reflux. A mixture containing acrylic acid (10 grams), deionised water (40 grams), and potassium persulphate (0.5 grams) was prepared separately, and was added to the VDPA over 2.5 hours. The reaction mixture was maintained at this temperature for 2 hours.

The resultant solution was found to consist essentially of a copolymer of VDPA and acrylic acid, as shown by $^{31}$P N.M.R.

EXAMPLE 3

Synthesis of cross-linked poly(vinylidene-1,1-diphosphonic acid-co-acrylic acid)

A resin pot fitted with a thermometer, a condenser, a nitrogen outlet a stirrer, an addition funnel, and a nitrogen inlet was flushed with nitrogen for 30 minutes.

Vinylidene-1,1-diphosphonic acid (6.8 grams), and deionised water (40 grams) was added to the vessel. The reaction vessel was heated in an oil bath set at 110° C. until the reflux temperature was attained. The contents were maintained at reflux. A mixture containing acrylic acid (10 grams), deionised water (40 grams), divinyl benzene (0.2 grams), and potassium persulphate (0.5 grams) was prepared separately, and was added to the VDPA over 2.5 hours. The reaction mixture was maintained at this temperature for 2 hours.

A phosphorus-containing insoluble copolymer of VDPA and AA was obtained.

EXAMPLE 4

Synthesis of poly(vinylidene-1,1-diphosphonic acid sodium salt-co-acrylic acid)

A resin pot fitted with a thermometer, a condenser, a nitrogen outlet a stirrer, an addition funnel, and a nitrogen inlet was flushed with nitrogen for 30 minutes.

The tetra-sodium salt of vinylidene-1,1-diphosphonic acid (10 grams), and deionised water (40 grams) were added to the vessel. The reaction vessel was heated in an oil bath set at 110° C. until the reflux temperature was attained. The contents were maintained at reflux. A mixture containing acrylic acid (5 grams), deionised water (30 grams), and potassium persulphate (0.5 grams) was prepared separately, and was added to the VDPA over 2.5 hours. The reaction mixture was maintained at this temperature for 2 hours.

The resultant solution was found to consist essentially of a copolymer of VDPA sodium salt and acrylic acid, as shown by $^{31}$P N.M.R., having a molecular weight of 8000 (as measured by gel-permeation chromatography).

EXAMPLE 5

Example 4 was repeated using only 5 grams of vinylidene-1,1-diphosphonic acid tetra sodium salt. The product was shown by $^{31}$P N.M.R. to be a copolymer. A molecular weight of 8300 was demonstrated by gel-permeation chromatography. A conversion rate of 90% was observed.

EXAMPLE 6

Synthesis of poly(vinylidene-1,1-diphosphonic acid-co-mono sodium maleate)

A resin pot fitted with a thermometer, a condenser, a nitrogen outlet, a stirrer, an addition funnel, and a nitrogen inlet was flushed with nitrogen for 30 minutes.

Maleic anhydride (5 grams), sodium hydroxide (2 grams), and deionised water (5 grams) were added to the reaction vessel. The reaction vessel was placed in an oil bath set at 130° C. and the contents maintained at this temperature for 30 minutes.

A mixture of vinylidene-1,1-diphosphonic acid (5 grams), potassium persulphate (1 gram), and deionised water (40 grams) was made separately, and charged to the reaction vessel over a period of 2.5 hours. The reaction mixture was maintained at this temperature for 3 hours.

The resultant solution was found to consist essentially of a copolymer of VDPA and mono-sodium maleate, as shown by $^{31}$P N.M.R.

EXAMPLES 7 AND 8

Synthesis of poly vinylidene-1,1-diphosphonic acid (PVDPA) in alcohols

The homo-polymerisation of vinylidene diphosphonic acid (VDPA) in alcohols is described in these examples.

The solvents used were methanol, ethanol and 1-butanol.

The free-radical initiators examined were 1,1-azobis (isobutyronitrile) (AIBN), benzoyl peroxide (BPO), di-(2-ethylhexyl) peroxydicarbonate (DEHPC) and t-butylperoxy-2-ethylhexanoate (TBPEH).

EXAMPLE 7

VDPA (1.88 g, 10.0 mmol) was dissolved in methanol (10 ml) and stirred at reflux (65° C.) under nitrogen for 30 minutes.

DEHPC (0.286 g, 1.00 mmol, 10 mol %) in methanol (5 ml) was added over 5 minutes. Approximately 10 minutes after addition of initiator was complete a white precipitate of poly(VDPA) began to appear. The polymerisation was left stirring at reflux for 4 hours after which time the mixture was cooled and filtered. Approximately 150 mg (8%) poly (VDPA) was obtained as a fine white precipitate. The filtrate was evaporated under reduced pressure producing a light brown oil (approximately 1.5 g). Analysis of both products showed no monomeric VDPA remained. Both products were found to be polymers of similar molecular weight (Mw approximately 800).

EXAMPLE 8

VDPA (3.76 g, 20.0 mmol) was dissolved in 1-butanol (10 ml) and stirred at reflux (116° C.) under nitrogen for 30 minutes. TBPEH (0.864 g, 4.00 mmol, 20 mol %) in 1-butanol (10 ml) was added over 3 hours. Approximately 20 minutes after addition of initiator was started a white precipitate of poly(VDPA) began to appear. The polymerisation was left stirring at reflux for 2 hours after which time the mixture was cooled and filtered. Approximately 350 mg (9%) poly(VDPA) was obtained as a fine white precipitate. The filtrate was evaporated under reduced pressure producing a light brown oil (approximately 3 g). Analysis of both products showed no monomeric VDPA remained. Both products were found to be polymers of similar molecular weight (Mw approximately 800).

EXAMPLES 9 TO 11

Copolymerisation of VDPA with Sodium Vinyl sulphonate: (SVS)

Three copolymers of vinylidene disphosphonic acid and sodium vinyl sulphonate were prepared.

Experimental methods

A 100 ml 3-necked round-bottomed flask was charged with vinylidene diphosphonic acid (VDPA) and water (see Table I below for quantities). This was heated at reflux (oil-bath temperature 110° C.), under nitrogen purge, for ½ hour and then an aqueous solution of sodium vinyl sulphonate (SVS) and potassium persulphate (KPS) was added continuously over 2½ hours. The reaction mixture was then held at reflux for a further two hours and then left to cool.

Table I, below, shows the quantities used in the individual Examples. The sodium vinyl sulphonate used was a 25% aqueous solution.

TABLE I

VDPA: SVS COPOLYMER PREPARATION

| EXAMPLE | VDPA:SVS ratio | IN FLASK VDPA (g) | IN FLASK water (ml) | ADDITION SOLUTION SVS (g) | ADDITION SOLUTION KPS (g) | ADDITION SOLUTION water (ml) |
|---|---|---|---|---|---|---|
| 9 | 1:1 | 10.0 | 10.0 | 27.6 | 2.0 | 10.0 |
| 10 | 1:2 | 5.0 | 10.0 | 27.6 | 2.0 | 10.0 |
| 11 | 1:2 | 5.0 | 10.0 | 27.6 | 1.0 | 10.0 |

These copolymers were worked-up to dry powders by evaporating down the reaction mixtures and then precipitating from methanol. The precipitates were then filtered and dried in a vacuum-oven.

Results

Table II, below, shows the composition analysis (via $^{31}P$ N.M.R.) and the molecular-weight analysis (via GPC).

TABLE II

ANALYSES

| EXAMPLE | Mw/g. mol-1 | % polymer | % residual monomer |
|---|---|---|---|
| 9 | 628 | 78.6 | 14.2 |
| 10 | 684 | 90.5 | 0.0 |
| 11 | 672 | 92.6 | 0.0 |

EXAMPLES 12 TO 17

Polymerisation of VDPA with two further monomeric species.

EXAMPLE 12

A polymer comprising VDPA, acrylic acid and acrylonitrile (molar ratio 1:1:1) was prepared as follows:

VDPA solution (approximately 14% w/w) was heated with potassium persulphate (KPS). A solution of the other two monomers (approximately 13% w/w) was added over 2.5 hours and the mixture refluxed for a further 2 hours.

EXAMPLE 13

A polymer comprising VDPA, the mono-sodium salt of vinyl sulphonic acid (Sodium VSA) and acrylic acid (molar ratio 1:1:1) was prepared as follows:

A solution of VDPA and sodium VSA (approximately 25% w/w) was charged to a flask and a solution of acrylic acid and KPS (approximately 13% w/w) as added over 2.5 hours. The mixture was refluxed for a further 2 hours.

EXAMPLE 14

A polymer comprising VDPA, sodium VSA and acrylic acid (molar ratio 1:4.5:4.5) was prepared by charging all the reactants, together with KPS, to a flask (as a 21% w/w solution) and heating the mixture for 5 hours.

EXAMPLE 15

A polymer comprising VDPA, sodium VSA and the sodium salt of acrylic acid (molar ratio 1:4.5:4.5) was prepared by the method of Example 14. Sufficient sodium hydroxide to neutralise the acrylic acid was added to the reaction mixture. The heating time was 5 hours.

EXAMPLE 16

A polymer comprising VDPA, sodium VSA and the sodium salt of acrylic acid (molar ratio 1:4.5:4.5) was prepared by the method of Example 14. The sodium salt of acrylic acid and KPS were added to the other reactants over 2.5 hours and the mixture heated for a further 4 hours.

EXAMPLE 17

A polymer comprising VDPA, sodium VSA and the sodium salt of acrylic acid (molar ratio 1:4.5:4.5) was prepared by the method of Example 16. A more concentrated solution of the sodium salt of acrylic acid was used and an extra charge of KPS added after 5 hours.

In the following Examples, the designations of materials used as scale/corrosion inhibitors are explained as follows:

| | |
|---|---|
| BRIQUEST[1]543-25S: | Essentially consists of a neutral aqueous sodium salt solution of diethylene-triamine-pentakis (methylene-phosphonic) acid, containing 25% by weight active acid. |
| 152DRW71: | Essentially consists of a copolymer of VDPA[2] and acrylic acid. |
| 152DRW80: | Essentially consists of a copolymer of VDPA[2] and maleic acid. |
| 176PDH106A: | Essentially consists of a homopolymer of VDPA[2]. |
| 152DRW91: | Essentially consists of a copolymer of VDPA[2] and vinyl sulphonic acid (1:1 molar). |
| 152DRW92:} 152DRW93:} | Essentially consists of a copolymer of VDPA[2] and vinyl sulphonic acid (1:2 molar). |
| 152DRW108: | Essentially consists of a copolymer of VDPA[2] and acrylamido methyl propane sulphonic acid (AMPS). |
| 152DRW111: | Essentially consists of a copolymer of VDPA[2] and AMPS. |
| 152DRW69: | Essentially consists of a copolymer of partially neutralised VDPA2 and acrylic acid. |

[1]BRIQUEST is a Registered Trade Mark.
[2]VDPA is vinylidene-1,1-di-phosphonic acid.

EXAMPLES 18 TO 20 (SCALE-INHIBITION; Bottle Tests).

These Examples illustrate the use of phosphonic acid polymers in the inhibition of barium sulphate scale formation.

A barium solution was prepared by dissolving 0.449 g/l barium chloride dihydrate ($BaCl_2.2H_2O$); and 1 g/l ammonium acetate ($CH_3CO_2NH_4$) in deionised water. A sulphate solution was also prepared by dissolving 3.34 g/l ammonium sulphate (($NH_4)_2SO_4$); and 1 g/l ammonium acetate ($CH_3CO_2NH_4$) in deionised water.

The barium and sulphate solutions were added to small bottles/jars in 25 ml aliquots. Sufficient inhibitor was added to the sulphate solutions to give concentrations of 50 to 100 ppm active acid once the barium and sulphate solutions had been mixed ie. 100 to 200 ppm of inhibitor was added to the sulphate solutions.

The pH of the barium and sulphate solutions (in the bottles/jars) was adjusted to either 6.5 or 4 pH at room temperature using HCl and NaOH. The barium and sulphate solutions in their bottles/jars were pre-warmed at 90° C. in an oven prior to mixing. Mixing proceeded as follows: the inhibited sulphate solution (25 mls) was poured into a barium solution jar (25 mls); then the combined barium and sulphate solution (50 mls) was poured back into the sulphate solution jar to aid mixing.

The combined solution was then returned to the oven (at 90° C.) and kept for either 4 or 24 hours. After this time the solution was quickly analysed for barium at 25° C. using a barium ion-selective electrode (which had been recently calibrated). A well-inhibited solution would not have any $BaSO_4$ forming and thus would leave all the $Ba^{2+}$ in solution. Conversely a solution which has a lot of $BaSO_4$ precipitate due to a poor inhibitor would have little $Ba^{2+}$ remaining in solution.

EXAMPLE 18

Results at 6.5 pH/90° C. using 50 ppm active acid of inhibitor: After 4 hours

| Inhibitor | ppm Ba2 + left in sln | % inhibition |
|---|---|---|
| Blank | 0.3 | 0 |
| BRIQUEST 543 | 5 | 40.9 |
| 152DRW71 | 3.6 | 36.3 |
| 152DRW80 | 12.1 | 52.9 |
| 176PDH106A | 10.7 | 51.1 |
| 152DRW91 | 15.6 | 56.3 |
| 152DRW92 | 6.2 | 43.7 |
| 152DRW93 | 8.1 | 47.4 |

Results at 6.5 pH/90° C. using 50 ppm active acid of inhibitor: After 24 hours

| Inhibitor | ppm Ba2 + left in sln | % inhibition |
|---|---|---|
| Blank | 0.5 | 0 |
| BRIQUEST 543 | 2.3 | 23.8 |
| 152DRW71 | 6 | 38.1 |
| 152DRW80 | 18.4 | 54.8 |
| 176PDH106A | 11.4 | 47.7 |
| 152DRW91 | 22.1 | 57.5 |
| 152DRW92 | 9.4 | 44.8 |
| 152DRW93 | 12.5 | 49 |

EXAMPLE 19

Results at 4 pH/90° C. using 50 ppm active acid of inhibitor: After 4 hours

| Inhibitor | ppm Ba2 + left in sln | % inhibition |
|---|---|---|
| Blank | 0.2 | 0 |
| BRIQUEST 543 | 0.2 | 0.9 |
| 152DRW71 | 5.6 | 43.8 |
| 152DRW80 | 0.4 | 10.2 |
| 176PDH106A | 19.9 | 60.6 |
| 152DRW91 | 4.3 | 40.4 |
| 152DRW92 | 0.3 | 6.7 |
| 152DRW93 | 0.3 | 4.5 |
| 152DRW108 | 0.5 | 11.2 |
| 152DRW111 | 0.2 | 0.1 |

Results at 4 pH/90° C. using 50 ppm active acid of inhibitor: After 24 hours

| Inhibitor | ppm Ba2 + left in sln | % inhibition |
|---|---|---|
| Blank | 0.2 | 0 |
| BRIQUEST 543 | 0.2 | 0.1 |
| 152DRW71 | 0.7 | 16.5 |
| 152DRW80 | 0.2 | 0.4 |
| 176PDH106A | 8.9 | 50 |
| 152DRW91 | 1.2 | 23.5 |
| 152DRW92 | 0.6 | 14.6 |
| 152DRW93 | 0.6 | 15 |
| 152DRW108 | 0.5 | 13 |
| 152DRW111 | 0.3 | 3.5 |

EXAMPLE 20

Results at 4 pH/90° C. using 100 ppm active acid of inhibitor: After 4 hours

| Inhibitor | ppm Ba2 + left in sln | % inhibition |
|---|---|---|
| Blank | 0.3 | 0 |
| BRIQUEST 543 | 0.1 | 0 |
| 152DRW71 | 3.4 | 35.5 |
| 152DRW80 | 1.4 | 23 |
| 176PDH106A | 19.3 | 59.1 |
| 152DRW91 | 21.5 | 60.5 |
| 152DRW92 | 2.8 | 32.9 |
| 152DRW93 | 5 | 40.7 |
| 152DRW108 | 1.3 | 22.5 |
| 152DRW111 | 0.4 | 0.1 |

Results at 4 pH/90° C. using 100 ppm active acid of inhibitor: After 24 hours

| Inhibitor | ppm Ba2 + left in sln | % inhibition |
|---|---|---|
| Blank | 0.3 | 0 |
| BRIQUEST 543 | 0.2 | 0 |
| 152DRW71 | 5.8 | 40.7 |
| 152DRW80 | 1.8 | 24.4 |
| 176PDH106A | 25.2 | 61.5 |
| 152DRW91 | 9.6 | 47.9 |
| 152DRW92 | 1.5 | 22.1 |
| 152DRW93 | 2.9 | 30.8 |
| 152DRW108 | 1.6 | 22.8 |
| 152DRW111 | 0.4 | 0.1 |

EXAMPLE 21 (SCALE INHIBITION; Tube Blocking Test)

A barium solution was prepared by dissolving 0.449 g/l barium chloride dihydrate; 50 g/l sodium chloride (NaCl); and 1 g/l ammonium acetate ($CH_3CO_2NH_4$) in deionised water.

Similarly a sulphate solution was prepared by dissolving 3.59 g/l sodium sulphate (Na$_2$SO$_4$); 50 g/l sodium chloride (NaCl); and 1 g/l ammonium acetate (CH$_3$CO$_2$NH$_4$) in deionised water. The inhibitor was added to the sulphate solution to obtain the desired level. The pH of the solutions was adjusted to 4.0 at room temperature. The solutions were then pumped through a fine capillary tube suspended in a waterbath at 90° C. The pressure along this capillary tube was then monitored. If any BaSO$_4$ had precipitated within the tube, blocking the tube, the pressure would subsequently have increased. The results below show the level of inhibitor required to prevent scale (and subsequent pressure rise) and the level of inhibitor which is sufficient to prevent scaling.

| Inhibitor | Level Insufficient to prevent Scaling/ ppm Active Acid | Level Sufficient to prevent Scaling/ ppm Active Acid |
|---|---|---|
| BRIQUEST 543 | 400 | 500 |
| 176PDH106A | 15 | 20 |
| 152DRW69 | 25 | 50 |
| 152DRW91 | 50 | 100 |
| 152DRW92 | 50 | 100 |
| 152DRW93 | 20 | 30 |

EXAMPLE 22 (Hydrolytic Stability Test)

A synthetic sea water (SMOW: Standard Mean Ocean Water) was made according to the following recipe in deionised water:

| | |
|---|---|
| NaCl | 24.53 g/l |
| MgCl$_2$.6H$_2$O | 11.105 g/l |
| Na$_2$SO$_4$ | 4.09 g/l |
| CaCl$_2$.2H$_2$O | 1.537 g/l |
| KCl | 0.695 g/l |
| KBr | 0.101 g/l |
| NaHCO$_3$ | 0.0954 g/l |

To this water 500 ppm active acid of inhibitor was added. The pH was then adjusted to 4 pH at room temperature using HCl. The solution was then introduced into a stainless steel bomb which was subsequently placed in an autoclave. The temperature was set to 200° C. Once at this temperature the pressure within the bomb was approximately 15.5 Bar (240 PSIG). The solution was continually stirred whilst inside the bomb. The test duration lasted roughly 5 days (approximately 140 hours) and during this time samples were taken every day. The samples were then analysed for orthophosphate and total phosphate content. If it is assumed that the polymer degradation produces orthophosphate, then monitoring the increase in "orthophosphate to total phosphate" ratio indicates the progress of that degradation.

The table below shows the orthophosphate to total phosphate ratios for two of the phosphonic acid polymers:

| 152DRW91 | | | | | |
|---|---|---|---|---|---|
| Time/hours | 0 | 24 | 48 | 72 | 136 |
| % Orthophosphate to total phosphate | 5.9 | n.d.* | 6.5 | 12.7 | 16.2 |

| 176PDH106A | | | | | |
|---|---|---|---|---|---|
| Time/hours | 0 | 24 | 48 | 72 | 136 |
| % Orthophosphate to total phosphate | 7.6 | 17 | 17.2 | 18 | 25.9 |

*not determined

EXAMPLE 23 (Corrosion Inhibition Test)

The corrosion rate of mild steel (C1018 grade) in water, with and without inhibitors, was assessed by an electrochemical method—Linear Polarisation Resistance (LPR). The medium used was South Staffs mains water adjusted to 7.5 pH after the inhibitor has been added. The solution was then placed in a waterbath set at 25° C. with constant stirring. Measurements were taken at half hourly intervals for several days. The averaged corrosion rates (in mm per year) for the first 20 hours are tabulated below:

| Sample | Average Corrosion Rate (mm/yr) |
|---|---|
| Blank ie. no inhibitor | 0.211 |
| 50 ppm 152DRW91 | 0.0175 |
| 50 ppm 152DRW92 | 0.0396 |
| 50 ppm 152DRW93 | 0.0533 |
| 50 ppm 176PDH106A | 0.0765 |
| 50 ppm 152DRW80 | 0.0813 |
| 50 ppm 152DRW69 | 0.157 |

Summarising the LPR (Linear Polarisation Resistance) corrosion inhibition screening test results, the compounds can be expressed in descending order of inhibition potential

| "BEST" | | | | | "WORST" |
|---|---|---|---|---|---|
| 152DRW91 > 152DRW92 > 152DRW93 | | > 176PDH106 | > 152DRW80 | > | 152DRW69 |
| Vinyl Sulphonic Acid Copolymers | | Poly (VDPA) | Maleic copolymer | | Acrylic Copolymer |

However even 50 ppm active acid of the "worst" sample (152DRW69; the Acrylic acid copolymer of VDPA) gives some corrosion inhibition (0.158 mm/yr corrosion rate) over the blank whose corrosion rate was 0.211 mm/yr. It is quite possible that the addition of more copolymer would have a greater inhibitory affect. Using a typical dose of 50 ppm, of the vinyl sulphonate copolymer (152DRW91) gives a low corrosion rate of 0.0175 mm/yr and hence good corrosion inhibition.

EXAMPLE 24 (SCALE INHIBITION: pH-drop Test)

Calcium carbonate (calcite form) scale inhibition was assessed by a 'pH drop' test. The basis of this test is that precipitation of CaCO$_3$ removes CO$_3^{2-}$ from solution with a consequent drop in pH. Effective inhibitors are capable of maintaining CaCO$_3$ in supersaturated solution (as indicated by little or no decrease in pH with time) whereas poor inhibition is characterised by a rapid drop in solution pH towards the saturation value.

This test is performed using a synthetic water which is made by mixing equal amounts (250 ml) of $Ca^{2+}$ solution and a $HCO_3^-$ solution. The $Ca^{2+}$ solution is prepared by dissolving 1.174 g/l $CaCl_2.2H_2O$ in deionised water whilst the $HCO_3^-$ solution is prepared by dissolving 1.008 g/l $NaHCO_3$ in deionised water. Once the solutions are mixed together and inhibitor is added the flask is immersed in a waterbath set at 60° C. and the pH is adjusted to 8.65 pH at 60° C. The test continues for 1 hour once the mixed solution has reached 60° C. The solution is constantly stirred and the pH is constantly monitored. The inhibitor levels evaluated were 5 and 10 ppm (as active acid). The table below shows the results. 100% inhibition is said to occur when no drop in pH is noticed.

| Sample Code | Dose* | pH after 1 hr |
|---|---|---|
| Blank | 0 | 7.80 |
| 176PDH106A | 5 ppm | 8.46 |
| 152DRW91 | 5 ppm | 8.46 |
| 152DRW92 | 5 ppm | 8.48 |
| 152DRW93 | 5 ppm | 8.52 |
| 176PDH106A | 10 ppm | 8.57 |
| 152DRW91 | 10 ppm | 8.68 |
| 152DRW92 | 10 ppm | 8.60 |
| 152DRW93 | 10 ppm | 8.68 |

*ppm active acid.

We claim:

1. A method for the treatment of an aqueous liquid containing at least 200 ppm total hardness expressed as calcium carbonate, and having a maximum pH of 8.5 to inhibit the formation of insoluble divalent or trivalent metal salts in said liquid, wherein said method comprises adding to said liquid an effective amount of up to 100 ppm of said liquid of a polymer selected from the group consisting of:
   (a) homopolymers of di-phosphonic acids or of fully or partly neutralised salts of said acids containing at least one unsaturated carbon-to-carbon bond;
   (b) co-polymers of di-phosphonic acids or of fully or partly neutralised salts of said acids containing at least one unsaturated carbon-to-carbon bond and a further compound containing at least one unsaturated carbon-to-carbon bond; and
   (c) terpolymers of di-phosphonic acids, or of fully or partly neutralised salts of said acids, containing at least one unsaturated carbon-to-carbon bond and two further compounds, each of said two further compounds containing at least one unsaturated carbon-to-carbon bond.

2. The method of claim 1, wherein said aqueous liquid has a maximum pH of 8.0.

3. The method of claim 1, wherein said aqueous liquid has a pH in the range of 1.0 to 7.0.

4. The method of claim 3, wherein said aqueous liquid has a pH in the range 3.5 to 6.5.

5. The method of claim 1, wherein said insoluble metal salts are selected from the group consisting of barium sulphate and calcium carbonate.

6. The method of claim 1, wherein said insoluble metal salts are selected from the group consisting of calcium sulphate, strontium sulphate, radium sulphate, lead sulphate and mixtures of any two or more of said sulphates.

7. The method of claim 1, wherein said phosphonic acid is vinylidene-1,1-di-phosphonic acid.

8. The method of claim 1, wherein said phosphonic acid salt is selected from the group consisting of mono-, di-, tri- and tetra-alkali metal salts of vinylidene-1,1-diphosphonic acid.

9. The method of claim 8, wherein said phosphonic acid salt is selected from the group consisting of the mono-, di-, tri- and tetra-sodium salts of vinylidene-1,1-diphosphonic acid.

10. The method of claim 1, wherein said at least one further compound is selected from the group consisting of unsaturated carboxylic acids, partly neutralised metal salts of said acids and fully neutralised metal salts of said acids.

11. The method of claim 10, wherein said unsaturated carboxylic acid is selected from the group consisting of vinyl phosphonic acid, acrylic acid, methacrylic acid, maleic acid and mono- or di-sodium salts of said acids.

12. The method of claim 1, wherein said at least one further compound is selected from the group consisting of mono- or polyfunctional sulphonic acids containing one or more unsaturated carbon-to-carbon bonds and fully or partly neutralised salt of said acids.

13. The method of claim 12, wherein said sulphonic acid is selected from the group consisting of vinyl sulphonic acid (VSA), acrylamido methyl propane sulphonic acid (AMPS), and a fully or partly neutralised salt of either of said acids.

14. The method of claim 13, wherein the molar ratio of said vinylidene-1,1-diphosphonic acid to said VSA or said AMPS is in the range 1:99 to 99:1.

15. The method of claim 14, wherein said ratio is 50:50.

16. The method of claim 14, wherein said ratio is 33:66.

17. The method of claim 14, wherein said ratio is 10:90.

18. The method of claim 1, wherein said polymer consists essentially of poly(vinylidene-1,1-diphosphonic acid).

19. The method of claim 1, wherein said polymer consists essentially of a salt selected from the group consisting of mono-, di-, tri- and tetra-sodium salts of poly(vinylidene-1,1-di-phosphonic acid).

20. The method of claim 1, wherein said polymer consists essentially of a copolymer of vinylidene-1,1-di-phosphonic acid and acrylic acid.

21. The method of claim 1, wherein said polymer consists essentially of a copolymer of a sodium salt of vinylidene-1,1-di-phosphonic acid and acrylic acid.

22. The method of claim 1, wherein said polymer consists essentially of a copolymer of vinylidene-1,1-di-phosphonic acid and maleic acid.

23. The method of claim 1, wherein said polymer consists essentially of a copolymer of vinylidene-1,1-di-phosphonic acid and mono-sodium maleate.

24. The method of claim 1, wherein said polymer consists essentially of a cross-linked copolymer of vinylidene-1,1-diphosphonic acid and acrylic acid.

25. The method of claim 1, wherein said polymer consists essentially of a terpolymer of vinylidene-1,1-diphosphonic acid, vinyl sulphonic acid and a compound selected from the group consisting of vinyl phosphonic acid, acrylic acid, methacrylic acid, maleic acid, fully or partly neutralised salts of said acids, and acrylonitrile.

* * * * *